(12) United States Patent
Imoto

(10) Patent No.: US 10,071,044 B2
(45) Date of Patent: Sep. 11, 2018

(54) THICKENED COMPOSITION CONTAINING LIPID PEPTIDE-TYPE COMPOUND

(71) Applicant: NISSAN CHEMICAL INDUSTRIES, LTD., Tokyo (JP)

(72) Inventor: Takayuki Imoto, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/305,437

(22) PCT Filed: May 14, 2015

(86) PCT No.: PCT/JP2015/063933
§ 371 (c)(1),
(2) Date: Oct. 20, 2016

(87) PCT Pub. No.: WO2015/174500
PCT Pub. Date: Nov. 19, 2015

(65) Prior Publication Data
US 2017/0042783 A1    Feb. 16, 2017

(30) Foreign Application Priority Data

May 15, 2014  (JP) ................................ 2014-101441

(51) Int. Cl.
| | | |
|---|---|---|
| A61K 8/64 | (2006.01) |
| A61K 8/36 | (2006.01) |
| A61K 8/67 | (2006.01) |
| A61K 47/22 | (2006.01) |
| A61K 47/18 | (2017.01) |
| A61K 47/10 | (2017.01) |
| A61K 47/12 | (2006.01) |
| A61K 8/34 | (2006.01) |
| A61Q 19/00 | (2006.01) |
| A61K 47/34 | (2017.01) |
| A61K 9/08 | (2006.01) |
| A61K 47/42 | (2017.01) |

(52) U.S. Cl.
CPC ............ *A61K 8/64* (2013.01); *A61K 8/345* (2013.01); *A61K 8/361* (2013.01); *A61K 8/676* (2013.01); *A61K 9/08* (2013.01); *A61K 47/10* (2013.01); *A61K 47/12* (2013.01); *A61K 47/183* (2013.01); *A61K 47/22* (2013.01); *A61K 47/34* (2013.01); *A61K 47/42* (2013.01); *A61Q 19/00* (2013.01); *A61K 2800/10* (2013.01); *A61K 2800/48* (2013.01)

(58) Field of Classification Search
CPC .......... A61K 8/64; A61K 8/345; A61K 8/361; A61K 8/676; A61K 9/08; A61K 47/10; A61K 47/12; A61K 47/183; A61K 47/22; A61K 47/34; A61K 47/42; A61K 2800/10; A61K 2800/48; A61Q 19/00

USPC ........................................................ 514/773
See application file for complete search history.

(56) References Cited

U.S. PATENT DOCUMENTS

| | | | | |
|---|---|---|---|---|
| 2012/0258059 A1* | 10/2012 | Iwama | ..................... | A61K 8/64 424/59 |
| 2015/0250880 A1* | 9/2015 | Matsumoto | .............. | A61K 8/64 524/17 |

FOREIGN PATENT DOCUMENTS

| | | |
|---|---|---|
| EP | 2692335 A1 | 2/2014 |
| JP | 2007-501265 A | 1/2007 |
| JP | 2010-202522 A | 9/2010 |
| JP | 2011-195455 A | 10/2011 |
| JP | 2012-213657 A | 11/2012 |
| WO | 2004/105717 A1 | 12/2004 |
| WO | 2009/005152 A1 | 1/2009 |
| WO | 2010/013555 A1 | 2/2010 |
| WO | 2011/052613 A1 | 5/2011 |

(Continued)

OTHER PUBLICATIONS

Aug. 18, 2015 Written Opinion issued in International Patent Application No. PCT/JP2015/063933.

(Continued)

*Primary Examiner* — Kristin Ann Vajda
(74) *Attorney, Agent, or Firm* — Oliff PLC

(57) ABSTRACT

A thickened composition that does not lose viscosity even in the presence of an organic acid. A thickened composition, including a polyhydric alcohol, water, an organic acid, and a lipid peptide-type compound containing at least one of a compound of Formula (1) to Formula (3) below and a pharmaceutically usable salt of compound of Formula (1) to Formula (3), (1)

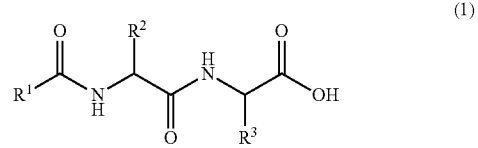

where $R^1$ is a $C_{9-23}$ aliphatic group, $R^2$ is a hydrogen atom or a $C_{1-4}$ alkyl group that optionally has a $C_{1-2}$ branched chain, $R^3$ is a $-(CH_2)_n-X$ group, n is a number of 1 to 4, X is an amino group, guanidino group, $-CONH_2$ group, a 5-membered ring group optionally containing 1 to 3 nitrogen atom(s), a 6-membered ring group optionally containing 1 to 3 nitrogen atom(s), or a condensed heterocycle group that contains a 5-membered ring and a 6-membered ring optionally containing 1 to 3 nitrogen atom(s).

5 Claims, No Drawings

(56) References Cited

FOREIGN PATENT DOCUMENTS

WO 2014/003015 A1 1/2014
WO 2014/054702 A1 4/2014

OTHER PUBLICATIONS

Aug. 18, 2015 International Search Report issued in International Patent Application No. PCT/JP2015/063933.
Dec. 8, 2017 extended European Search Report Issued in European Patent Application No. 15792809.4.

\* cited by examiner

THICKENED COMPOSITION CONTAINING LIPID PEPTIDE-TYPE COMPOUND

TECHNICAL FIELD

The present invention relates to a thickened composition containing a lipid peptide-type compound, and in particular, to a thickened composition for external skin application containing the lipid peptide-type compound.

BACKGROUND ART

In an external skin composition contained in a biomedical material or a cosmetic product, various salts are sometimes added as a moisturizer, a bleaching agent, an amino acid, and a vitamin. Therefore, in applications in the field of cosmetics, a salt-tolerant thickening composition needs to be developed that does not lose viscosity even in the presence of these salts. In Patent Document 1, for example, salt tolerance is obtained by crosslinking hyaluronic acid, which is a polymer. However, the crosslinking may impair one of the important features of a cosmetic product, namely, the feel in use (spreadability of the product). On the other hand, in recent years, a low-molecular gelator has been receiving attention, as a gelator composition wherein the viscosity of which can be increased so as to thicken a cosmetic product without impairing the feel in use of the product (spreadability of the product) (Patent Documents 2 and 3). These documents, however, do not discuss salt tolerance.

PRIOR ART DOCUMENTS

Patent Documents

Patent Document 1: Japanese Patent Application Publication No. 2010-202522 (JP 2010-202522 A)
Patent Document 2: Japanese Patent Application Publication No. 2012-213657 (JP 2012-213657 A)
Patent Document 3: International Publication No. WO 2011/052613 Pamphlet

SUMMARY OF THE INVENTION

Problem to be Solved by the Invention

The present invention is devised based on the above circumstances, and the object of the present invention is to provide a thickened composition that does not lose viscosity even in the presence of an organic acid such as ascorbic acid or a salt thereof.

Means for Solving the Problem

The inventor of the present invention has conducted intensive research to obtain a composition that can be thickened even in the presence of a high concentration of an organic acid or a salt thereof. As a result, the inventor has found that, by combining a lipid peptide-type compound that includes a low-molecular lipid peptide or a pharmaceutically usable salt thereof, water, a polyhydric alcohol, and an organic acid together, a composition can be obtained that can be thickened even in the presence of an organic acid or a salt thereof at a high concentration at which no conventional, already-existing thickener can exhibit its thickening ability. Thus, the present invention has now been completed.

Thus, the present invention relates to: as a first aspect, a thickened composition, comprising:
a polyhydric alcohol;
water;
an organic acid; and
a lipid peptide-type compound containing at least one of a compound of Formula (1) to Formula (3) below and a pharmaceutically usable salt of the compound of Formula (1) to Formula (3):

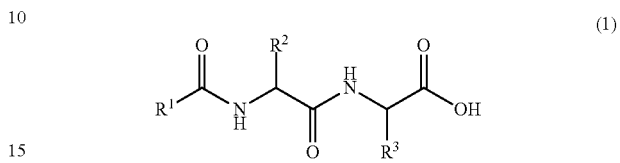

(where $R^1$ is a $C_{9\text{-}23}$ aliphatic group, $R^2$ is a hydrogen atom or a $C_{1\text{-}4}$ alkyl group that optionally has a $C_{1\text{-}2}$ branched chain, $R^3$ is a $-(CH_2)_n-X$ group, n is a number of 1 to 4, X is an amino group, a guanidino group, a $-CONH_2$ group, a 5-membered ring group optionally containing 1 to 3 nitrogen atom(s), a 6-membered ring group optionally containing 1 to 3 nitrogen atom(s), or a condensed heterocycle group that contains a 5-membered ring and a 6-membered ring optionally containing 1 to 3 nitrogen atom(s))

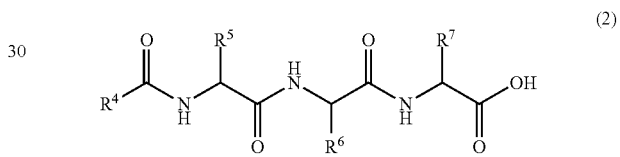

(where $R^4$ is a $C_{9\text{-}23}$ aliphatic group, $R^5$ to $R^7$ are each independently a hydrogen atom, a $C_{1\text{-}4}$ alkyl group that optionally has a $C_{1\text{-}2}$ branched chain, or a $-(CH_2)_n-X$ group, n is a number of 1 to 4, X is an amino group, a guanidino group, a $-CONH_2$ group, a 5-membered ring group optionally containing 1 to 3 nitrogen atom(s), a 6-membered ring group optionally containing 1 to 3 nitrogen atom(s), or a condensed heterocycle group that contains a 5-membered ring and a 6-membered ring optionally containing 1 to 3 nitrogen atom(s))

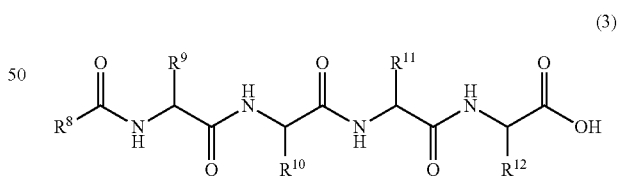

(where $R^8$ is a $C_{9\text{-}23}$ aliphatic group, $R^9$ to $R^{12}$ are each independently a hydrogen atom, a $C_{1\text{-}4}$ alkyl group that optionally has a $C_{1\text{-}2}$ branched chain, or a $-(CH_2)_n-X$ group, n is a number of 1 to 4, X is an amino group, a guanidino group, a $-CONH_2$ group, a 5-membered ring group optionally containing 1 to 3 nitrogen atom(s), a 6-membered ring group optionally containing 1 to 3 nitrogen atom(s), or a condensed heterocycle group that contains a 5-membered ring and a 6-membered ring optionally containing 1 to 3 nitrogen atom(s));

as a second aspect, the thickened composition according to the first aspect, further comprising at least one fatty acid;

as a third aspect, the thickened composition according to the first aspect or the second aspect, further comprising at least one surfactant;

as a fourth aspect, the thickened composition according to the second aspect, wherein the fatty acid is stearic acid;

as a fifth aspect, the thickened composition according to the third aspect, wherein the surfactant is one or more compound(s) selected from the group consisting of ethylene glycol alkyl ethers;

as a sixth aspect, the thickened composition according to any one of the first aspect to the fifth aspect, wherein the organic acid is ascorbic acid;

as a seventh aspect, a feedstock premix for preparation of the thickened composition as described in any one of the first aspect to the sixth aspect, comprising:
a polyhydric alcohol;
water; and
a lipid peptide-type compound containing at least one of a compound of Formula (1) to Formula (3) below and a pharmaceutically usable salt of the compound of Formula (1) to Formula (3):

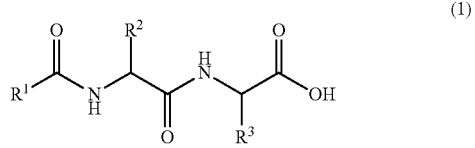

(1)

(where $R^1$ is a $C_{9-23}$ aliphatic group, $R^2$ is a hydrogen atom or a $C_{1-4}$ alkyl group that optionally has a $C_{1-2}$ branched chain, $R^3$ is a —$(CH_2)_n$—X group, n is a number of 1 to 4, X is an amino group, a guanidino group, a —$CONH_2$ group, a 5-membered ring group optionally containing 1 to 3 nitrogen atom(s), a 6-membered ring group optionally containing 1 to 3 nitrogen atom(s), or a condensed heterocycle group that contains a 5-membered ring and a 6-membered ring optionally containing 1 to 3 nitrogen atom(s))

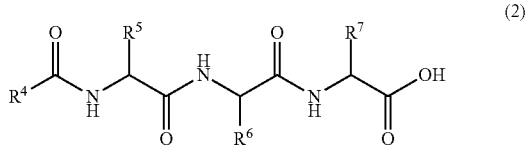

(2)

(where $R^4$ is a $C_{9-23}$ aliphatic group, $R^5$ to $R^7$ are each independently a hydrogen atom, a $C_{1-4}$ alkyl group that optionally has a $C_{1-2}$ branched chain, or a —$(CH_2)_n$—X group, n is a number of 1 to 4, X is an amino group, a guanidino group, a —$CONH_2$ group, a 5-membered ring group optionally containing 1 to 3 nitrogen atom(s), a 6-membered ring group optionally containing 1 to 3 nitrogen atom(s), or a condensed heterocycle group that contains a 5-membered ring and a 6-membered ring optionally containing 1 to 3 nitrogen atom(s))

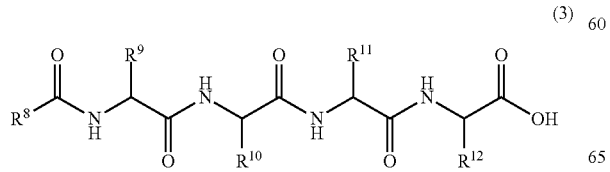

(3)

(where $R^8$ is a $C_{9-23}$ aliphatic group, $R^9$ to $R^{12}$ are each independently a hydrogen atom, a $C_{1-4}$ alkyl group that optionally has a $C_{1-2}$ branched chain, or a —$(CH_2)_n$—X group, n is a number of 1 to 4, X is an amino group, a guanidino group, a —$CONH_2$ group, a 5-membered ring group optionally containing 1 to 3 nitrogen atom(s), a 6-membered ring group optionally containing 1 to 3 nitrogen atom(s), or a condensed heterocycle group that contains a 5-membered ring and a 6-membered ring optionally containing 1 to 3 nitrogen atom(s)); and as an eighth aspect, the premix according to the seventh aspect, further comprising at least one fatty acid.

Effects of Invention

The present invention can provide a composition that can be thickened even in the presence of an organic acid or a salt thereof at a high concentration at which no conventional, already-existing thickener can exhibits its thickening ability.

In addition, the lipid peptide compound contained in the thickened composition of the present invention is an artificial low-molecular compound that is composed solely of a lipid and a peptide and is very safe. Furthermore, various components contained as additives in the thickened composition of the present invention are additives that are generally used as additives in food, cosmetics, and pharmaceuticals.

In other words, the thickened composition of the present invention is highly safe for living organisms, and highly useful particularly in applications such as biomedical materials or cosmetics materials, when considering the high safety level required in these applications.

MODES FOR CARRYING OUT THE INVENTION

The present invention relates to a thickened composition that comprises a polyhydric alcohol, water, an organic acid, and a lipid peptide-type compound containing at least one of a compound of Formula (1) to Formula (3) below and a pharmaceutically usable salt thereof, and, when desired, also comprises a fatty acid, a surfactant, and other additives.

Each component will be described below.

[Lipid Peptide-Type Compound]

The lipid peptide-type compound used in the thickened composition of the present invention can be a compound of Formula (1) to Formula (3) below (lipid peptide) or a pharmaceutically usable salt thereof (a low-molecular compound having a lipid moiety serving as a hydrophobic moiety and a peptide moiety serving as a hydrophilic moiety).

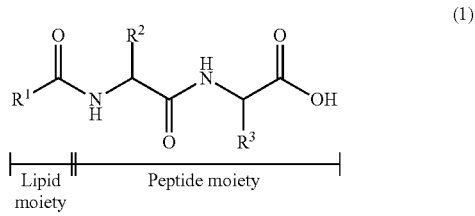

(1)

In Formula (1) above, $R^1$ is a $C_{9-23}$ aliphatic group and is preferably a linear aliphatic group having a carbon atom number of 11 to 23 that optionally contains 0 to 2 unsaturated bond(s).

Specific examples of the lipid moiety (acyl group) including $R^1$ and an adjacent carbonyl group include lauroyl group, dodecylcarbonyl group, myristoyl group, tetradecylcarbonyl group, palmitoyl group, margaroyl group, oleoyl group, elaidoyl group, linoleoyl group, stearoyl group, vaccenoyl group, octadecylcarbonyl group, arachidoyl group, eicosylcarbonyl group, behenoyl group, erucanoyl group, docosylcarbonyl group, lignoceroyl group, and nervonoyl group. Particularly preferable examples thereof include lauroyl group, myristoyl group, palmitoyl group, margaroyl group, stearoyl group, oleoyl group, elaidoyl group, and behenoyl group.

In Formula (1) above, $R^2$ in the peptide moiety is a hydrogen atom or a $C_{1-4}$ alkyl group that optionally contains a $C_{1-2}$ branched chain.

The $C_{1-4}$ alkyl group that optionally contains a $C_{1-2}$ branched chain means an alkyl group that contains a $C_{1-4}$ main chain and optionally contains a $C_{1-2}$ branched chain, and specific examples thereof include methyl group, ethyl group, n-propyl group, i-propyl group, n-butyl group, i-butyl group, sec-butyl group, and tert-butyl group.

$R^2$ is preferably a hydrogen atom or a $C_{1-3}$ alkyl group that optionally contains a $C_1$ branched chain, and is more preferably a hydrogen atom.

The $C_{1-3}$ alkyl group that optionally contains a $C_1$ branched chain means an alkyl group that contains a $C_{1-3}$ main chain and optionally contains a $C_1$ branched chain, and specific examples thereof include methyl group, ethyl group, n-propyl group, i-propyl group, i-butyl group, and sec-butyl group. Methyl group, i-propyl group, i-butyl group, and sec-butyl group are preferable.

In Formula (1) above, $R^3$ is a —$(CH_2)_n$—X group. In the —$(CH_2)$n-X group, n is a number of 1 to 4, and X is an amino group, a guanidino group, a —$CONH_2$ group, a 5-membered ring group optionally containing 1 to 3 nitrogen atom(s), a 6-membered ring group optionally containing 1 to 3 nitrogen atom(s), or a condensed heterocycle group that contains a 5-membered ring and a 6-membered ring optionally containing 1 to 3 nitrogen atom(s).

In the —$(CH_2)_n$—X group as $R^3$, X is preferably an amino group, a guanidino group, a carbamoyl group (—$CONH_2$ group), a pyrrole group, an imidazole group, a pyrazole group, or an indole group, and is more preferably an imidazole group. In the —$(CH_2)_n$—X group, n is preferably 1 or 2 and is more preferably 1.

Accordingly, the —$(CH_2)_n$—X group is preferably an aminomethyl group, a 2-aminoethyl group, a 3-aminopropyl group, a 4-aminobutyl group, a carbamoylmethyl group, a 2-carbamoylethyl group, a 3-carbamoylbutyl group, a 2-guanidinoethyl group, a 3-guanidinobutyl group, a pyrrole methyl group, a 4-imidazole methyl group, a pyrazole methyl group, or a 3-indole methyl group, is more preferably a 4-aminobutyl group, a carbamoylmethyl group, a 2-carbamoylethyl group, a 3-guanidinobutyl group, a 4-imidazole methyl group, or a 3-indole methyl group, and is further preferably a 4-imidazole methyl group.

Lipid peptides that are particularly preferable as a lipid peptide-type compound in the compound of Formula (1) above are the following compounds formed from a lipid moiety and a peptide moiety (a moiety of assembled amino acids) (amino acid abbreviations are as follows: alanine (Ala), asparagine (Asn), glutamine (Gln), glycine (Gly), histidine (His), isoleucine (Ile), leucine (Leu), lysine (Lys), tryptophan (Trp), and valine (Val)): lauroyl-Gly-His, lauroyl-Gly-Gln, lauroyl-Gly-Asn, lauroyl-Gly-Trp, lauroyl-Gly-Lys, lauroyl-Ala-His, lauroyl-Ala-Gln, lauroyl-Ala-Asn, lauroyl-Ala-Trp, and lauroyl-Ala-Lys; myristoyl-Gly-His, myristoyl-Gly-Gln, myristoyl-Gly-Asn, myristoyl-Gly-Trp, myristoyl-Gly-Lys, myristoyl-Ala-His, myristoyl-Ala-Gln, myristoyl-Ala-Asn, myristoyl-Ala-Trp, and myristoyl-Ala-Lys; palmitoyl-Gly-His, palmitoyl-Gly-Gln, palmitoyl-Gly-Asn, palmitoyl-Gly-Trp, palmitoyl-Gly-Lys, palmitoyl-Ala-His, palmitoyl-Ala-Gln, palmitoyl-Ala-Asn, palmitoyl-Ala-Trp, and palmitoyl-Ala-Lys; and stearoyl-Gly-His, stearoyl-Gly-Gln, stearoyl-Gly-Asn, stearoyl-Gly-Trp, stearoyl-Gly-Lys, stearoyl-Ala-His, stearoyl-Ala-Gln, stearoyl-Ala-Asn, stearoyl-Ala-Trp, and stearoyl-Ala-Lys.

The most preferable examples thereof include lauroyl-Gly-His, lauroyl-Ala-His, myristoyl-Gly-His, myristoyl-Ala-His, palmitoyl-Gly-His, palmitoyl-Ala-His, stearoyl-Gly-His, and stearoyl-Ala-His.

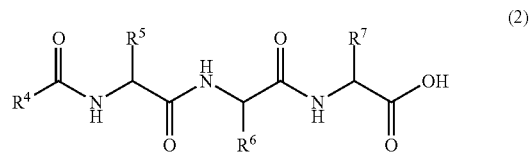

(2)

In Formula (2) above, $R^4$ is a $C_{9-23}$ aliphatic group. Preferable specific examples thereof include the same groups as defined above for $R^1$.

In Formula (2) above, $R^5$ to $R^7$ are each independently a hydrogen atom, a $C_{1-4}$ alkyl group that optionally has a $C_{1-2}$ branched chain, or a —$(CH_2)_n$—X group. It is preferable that at least one of $R^5$ to $R^7$ is a —$(CH_2)_n$—X group. n is a number of 1 to 4. X is an amino group, a guanidino group, a —$CONH_2$ group, a 5-membered ring group optionally containing 1 to 3 nitrogen atom(s), a 6-membered ring group optionally containing 1 to 3 nitrogen atom(s), or a condensed heterocycle group that contains a 5-membered ring and a 6-membered ring optionally containing 1 to 3 nitrogen atom(s). Preferable specific examples of $R^5$ to $R^7$ include the same groups as defined above for $R^2$ and $R^3$.

Lipid peptides that are preferable in a compound of Formula (2) above are the following compounds formed from a lipid moiety and a peptide moiety (a moiety of assembled amino acids): myristoyl-Gly-Gly-His, myristoyl-Gly-Gly-Gln, myristoyl-Gly-Gly-Asn, myristoyl-Gly-Gly-Trp, myristoyl-Gly-Gly-Lys, myristoyl-Gly-Ala-His, myristoyl-Gly-Ala-Gln, myristoyl-Gly-Ala-Asn, myristoyl-Gly-Ala-Trp, myristoyl-Gly-Ala-Lys, myristoyl-Ala-Gly-His, myristoyl-Ala-Gly-Gln, myristoyl-Ala-Gly-Asn, myristoyl-Ala-Gly-Trp, myristoyl-Ala-Gly-Lys, myristoyl-Gly-His-Gly, myristoyl-His-Gly-Gly, palmitoyl-Gly-Gly-His, palmitoyl-Gly-Gly-Gln, palmitoyl-Gly-Gly-Asn, palmitoyl-Gly-Gly-Trp, palmitoyl-Gly-Gly-Lys, palmitoyl-Gly-Ala-His, palmitoyl-Gly-Ala-Gln, palmitoyl-Gly-Ala-Asn, palmitoyl-Gly-Ala-Trp, palmitoyl-Gly-Ala-Lys, palmitoyl-Ala-Gly-His, palmitoyl-Ala-Gly-Gln, palmitoyl-Ala-Gly-Asn, palmitoyl-Ala-Gly-Trp, palmitoyl-Ala-Gly-Lys, palmitoyl-Gly-His-Gly, and palmitoyl-His-Gly-Gly.

Among them, lauroyl-Gly-Gly-His, myristoyl-Gly-Gly-His, palmitoyl-Gly-Gly-His, palmitoyl-Gly-His-Gly, palmitoyl-His-Gly-Gly, and stearoyl-Gly-Gly-His are the most preferable.

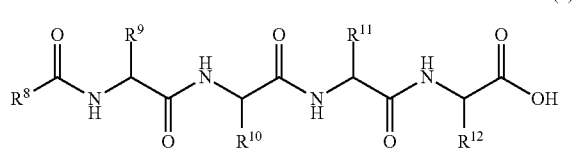

(3)

In Formula (3) above, $R^8$ is a $C_{9\text{-}23}$ aliphatic group. Preferable specific examples thereof include the same groups as defined above for $R^1$.

In Formula (3) above, $R^9$ to $R^{12}$ are each independently a hydrogen atom, a $C_{1\text{-}4}$ alkyl group that optionally has a $C_{1\text{-}2}$ branched chain, or a —$(CH_2)_n$—X group. Preferably, at least one of $R^9$ to $R^{12}$ is a —$(CH_2)_n$—X group. n is a number of 1 to 4. X is an amino group, a guanidino group, a —$CONH_2$ group, a 5-membered ring group optionally containing 1 to 3 nitrogen atom(s), a 6-membered ring group optionally containing 1 to 3 nitrogen atom(s), or a condensed heterocycle group that contains a 5-membered ring and a 6-membered ring optionally containing 1 to 3 nitrogen atom(s). Preferable specific examples of $R^9$ to $R^{12}$ include the same groups as defined above for $R^2$ and $R^3$.

Therefore, examples of lipid peptides that are particularly preferable as a preferable lipid peptide-type compound in a compound of Formula (3) above include lauroyl-Gly-Gly-Gly-His, myristoyl-Gly-Gly-Gly-His, palmitoyl-Gly-Gly-Gly-His, palmitoyl-Gly-Gly-His-Gly, palmitoyl-Gly-His-Gly-Gly, palmitoyl-His-Gly-Gly-Gly, and stearoyl-Gly-Gly-Gly-His.

In the present invention, the amount of the lipid peptide-type compound to be added is preferably 0.1% by mass to 10% by mass, more preferably 0.1% by mass to 5% by mass, and further preferably 0.25% by mass to 1% by mass relative to the total mass of the resulting thickened composition.

The lipid peptide-type compound used in the present invention contains at least one of the compound of Formula (1) to Formula (3) above (lipid peptide) and a pharmaceutically usable salt thereof, and such compounds can be used singly or as a combination of two or more of these.

[Polyhydric Alcohol]

The polyhydric alcohol used in the thickened composition of the present invention is a compound containing two or more hydroxy group(s) per molecule, and such polyhydric alcohols can be used singly or as a combination of two or more of these. Examples of the polyhydric alcohol include glycerin, 1,2-pentanediol, 1,2-hexanediol, 1,2-octanediol and 1,2-decanediol, 1,3-butylene glycol, propylene glycol, 3-methyl-1,3-butanediol, 1,3-propanediol, 2-methyl-1,3-propanediol, trimethylolpropane, pentaerythritol, hexylene glycol, diglycerin, polyglycerin, diethylene glycol, polyethylene glycol, dipropylene glycol, and polypropylene glycol. Preferable examples thereof include 1,2-pentanediol, 1,2-hexanediol, and 1,2-octanediol. 1,2-pentanediol or 1,2-hexanediol is further preferable.

In the present invention, the amount of the polyhydric alcohol to be added is 0.1% by mass to 95% by mass, for example, preferably 0.1% by mass to 80% by mass, and more preferably 0.1% by mass to 50% by mass relative to the total mass of the resulting thickened composition.

[Organic Acid]

Examples of the organic acid include ascorbic acid, citric acid, lactic acid, glycolic acid, succinic acid, acetic acid, malic acid, tartaric acid, fumaric acid, phosphoric acid, hydrochloric acid, and sulfuric acid. Preferable examples thereof include ascorbic acid, citric acid, and lactic acid. More preferable examples thereof include ascorbic acid and citric acid.

In the present invention, the amount of the organic acid to be added is 0.01% by mass to 20% by mass, for example, preferably 0.01% by mass to 15% by mass, and more preferably 0.1% by mass to 10% by mass relative to the total mass of the resulting thickened composition.

[Fatty Acid]

The thickened composition of the present invention may further comprise a fatty acid. The fatty acid used in the present invention is preferably at least one selected from the group consisting of $C_{10\text{-}20}$ saturated fatty acids, $C_{10\text{-}20}$ unsaturated fatty acids, and salts of these fatty acids. Examples of the fatty acid include capric acid, undecanoic acid, lauric acid, tridecanoic acid, myristic acid, pentadecanoic acid, palmitic acid, margaric acid, and stearic acid. Further preferable examples thereof include capric acid, lauric acid, myristic acid, palmitic acid, and stearic acid.

In the present invention, the amount of the fatty acid to be added is preferably 0.01% by mass to 1% by mass, more preferably 0.01% by mass to 0.5% by mass, and further preferably 0.025% by mass to 0.1% by mass relative to the total mass of the resulting thickened composition.

The fatty acid used in the present invention is at least one selected from the group of fatty acids described above, and such fatty acids can be used singly or as a combination of two or more of these.

[Surfactant]

The surfactant used in the thickened composition of the present invention is preferably a compound that contains a hydrophilic moiety and a hydrophobic moiety in the molecule and that has a betaine structure in the hydrophilic moiety (hereinafter, also called a betaine-based compound), or an ethylene glycol alkyl ether.

The betaine-based compound that can be used is a betaine-based compound that is well known as an amphoteric surfactant, including N-alkyl-N,N-dimethylamino acid betaines such as lauryl dimethylaminoacetic acid betaine (lauryl betaine); fatty acid amide alkyl-N,N-dimethylamino acid betaines such as cocamide propyl betaine and lauramide propyl betaine; imidazoline-type betaines such as sodium cocoamphoacetate and sodium lauroamphoacetate; alkyl sulfobetaines such as laurylhydroxy sulfobetaine and alkyl dimethyltaurines; sulfuric acid-type betaines such as alkyl dimethylamino ethanol sulfuric acid esters; and phosphoric acid-type betaines such as alkyl dimethylamino ethanol phosphoric acid esters.

Examples of the betaine-based compound include glycerophospholipids such as phosphatidylcholine, phosphatidylethanolamine, phosphatidylserine, phosphatidylinositol, phosphatidylglycerol, diphosphatidylglycerol (cardiolipin), and phosphatidic acid; lysoglycerophospholipids such as lysophosphatidylcholine (lysolecithin), lysophosphatidyl ethanolamine, lysophosphatidylserine, lysophosphatidylinositol, lysophosphatidylglycerol, and lysophosphatidic acid; sphingophospholipids such as sphingomyelin; and hydrogenated products thereof. These phospholipids may be of animal origin or plant origin, such as ones derived from soybeans or egg yolk, or may be synthesized chemically or by an enzymatic method.

Among these, preferable examples of the betaine-based compound include lauryl dimethylaminoacetic acid betaine, lauryl amidopropyl betaine, laurylhydroxy sulfobetaine, stearyl betaine, lysophosphatidylcholine (lysolecithin), lysophosphatidylethanolamine, lysophosphatidylserine, lysophosphatidylinositol, lysophosphatidylglycerol, and lysophosphatidic acid, and further preferable examples include lysophosphatidylcholine (lysolecithin).

Examples of the ethylene glycol alkyl ether include polyoxyethylene lauryl ether, polyoxyethylene palmitoyl ether, and polyoxyethylene stearyl ether. Polyoxyethylene lauryl ether and polyoxyethylene stearyl ether are preferable.

In the present invention, the amount of the surfactant to be added is preferably 0.1% by mass to 10% by mass, more preferably 0.1% by mass to 5% by mass, and further preferably 0.25% by mass to 1% by mass relative to the total mass of the resulting thickened composition.

The surfactant used in the present invention is at least one from the group of surfactants described above, and such surfactants can be used singly or as a combination of two or more of these.

[Other Additives]

To a solid base material (or an aqueous solid composition, a solution, or a dispersion) for external skin application of the present invention, an additive generally usable as an additive for cosmetics and an additive for quasi drugs can be added where appropriate. Examples of additional ingredients such as physiologically active substances and functional substances formulated in external skin preparations such as cosmetics and quasi drugs include moisturizers and tactile-feeling enhancers; surfactants other than the ones described above; polymers, thickeners, and gelators; solvents and propellants; antioxidants; reducing agents; oxidizing agents; preservatives, antimicrobial agents, and antiseptics; chelating agents; pH-adjusters, acids, and alkalis; powders; inorganic salts; ultraviolet absorbers; skin-brightening agents; vitamins and derivatives thereof; hair growth-promoting agents, blood circulation-promoters, and stimulating agents; hormones; anti-wrinkle agents, anti-aging agents, tightening agents, cool-feeling agents, warm-feeling agents, wound-healing promoters, abirritants, analgesics, and cell activators; plant, animal, and microbial extracts; antipruritics; keratin-exfoliating/dissolving agents; antiperspirants; refrigerants; styptics; enzymes; nucleic acids; perfumes; coloring agents, colorants, dyes, and pigments; antiphlogistics and anti-inflammatory agents; anti-asthmatic agents, drugs for chronic obstructive pulmonary diseases, antiallergic agents, and immunomodulators; and anti-infective agents and antifungal agents.

Preferable examples of the moisturizers and the tactile-feeling enhancers include polyols and polymers thereof such as glycerin, 1,3-butylene glycol, propylene glycol, 3-methyl-1,3-butanediol, 1,3-propanediol, 2-methyl-1,3-propanediol, trimethylolpropane, pentaerythritol, hexylene glycol, diglycerin, polyglycerin, diethylene glycol, polyethylene glycol, dipropylene glycol, polypropylene glycol, and ethylene glycol-propylene glycol copolymers; glycol alkyl ethers such as diethylene glycol monoethyl ether (ethoxydiglycol), ethylene glycol monoethyl ether, ethylene glycol monobutyl ether, and diethylene glycol dibutyl ether; water-soluble esters such as polyglyceryl-10 (eicosane dioate/tetradecane dioate) and polyglyceryl-10 tetradecane dioate; sugar alcohols such as sorbitol, xylitol, erythritol, mannitol, and maltitol; saccharides and derivatives thereof such as glucose, fructose, galactose, mannose, threose, xylose, arabinose, fucose, ribose, deoxyribose, maltose, trehalose, lactose, raffinose, gluconic acid, glucuronic acid, cyclodextrins ($\alpha$-, $\beta$-, and $\gamma$-cyclodextrins, and modified cyclodextrins such as maltosyl cyclodextrin and hydroxyalkyl cyclodextrin), $\beta$-glucan, chitin, chitosan, heparin and heparin derivatives, pectin, arabinogalactan, dextrin, dextran, glycogen, ethyl glucoside, poly(glucosylethyl methacrylate), and (glucosylethyl methacrylate) copolymer; hyaluronic acid and sodium hyaluronate; sodium chondroitin sulfate; mucoitin sulfate, charonin sulfate, kerato sulfate, and dennatan sulfate; *Tremella fuciformis* extract and *Tremella fuciformis* polysaccharide; fucoidan; tuberose polysaccharide and natural polysaccharides; organic acids such as citric acid, tartaric acid, and lactic acid, and salts thereof; urea and derivatives thereof; 2-pyrrolidone-5-carboxylic acid, and salts thereof including sodium salt thereof; amino acids such as betaine (trimethylglycine), proline, hydroxyproline, arginine, lysine, serine, glycine, alanine, phenylalanine, tyrosine, $\beta$-alanine, threonine, glutamic acid, glutamine, asparagine, aspartic acid, cysteine, methionine, leucine, isoleucine, valine, tryptophan, histidine, and taurine, and salts thereof; protein peptides, and derivative thereof, such as collagen, fish collagen, atelocollagen, gelatin, elastin, peptides derived from decomposed collagen, hydrolyzed collagen, hydroxypropylammonium chloride hydrolyzed collagen, peptides derived from decomposed elastin, peptides derived from decomposed keratin, hydrolyzed keratin, peptides derived from decomposed conchiolin, hydrolyzed conchiolin, peptides derived from decomposed silk protein, hydrolyzed silk, sodium lauroyl hydrolyzed silk, peptides derived from decomposed soy protein, peptides derived from decomposed wheat protein, hydrolyzed wheat protein, peptides derived from decomposed casein, and acylated peptides; acylated peptides such as palmitoyl oligopeptide, palmitoyl pentapeptide, and palmitoyl tetrapeptide; silylated peptides; a culture medium of lactic acid bacteria, a yeast extract solution, an eggshell membrane protein, bovine submaxillary mucin, hypotaurine, sesame lignan glycoside, glutathione, albumin, and whey; choline chloride and phosphoryl choline; and animal and plant extract components such as a placenta extract solution, elastin, collagen, aloe extract, *Hamamelis virginiana* water, *Luffa cylindrica* water, *Chamomilla recutita* extract, licorice extract, *Symphytum officinale* extract, silk extract, *Rosa roxburghii* extract, *Achillea millefolium* extract, *Eucalyptus globulus* extract, and *Melilotus officinalis* extract, and ceramides such as natural ceramides (type 1, 2, 3, 4, 5, and 6), hydroxyceramide, pseudoceramide, sphingoglycolipid, ceramide-containing extracts, and glucosylceramide-containing extracts.

Preferable examples of the surfactants include anionic surfactants, nonionic surfactants, cationic surfactants, amphoteric surfactants, and polymer surfactants. Preferable examples of the surfactants are exemplified below. Preferable examples of the anionic surfactants include fatty acid salts such as potassium laurate and potassium myristate; alkyl sulfuric acid ester salts such as sodium lauryl sulfate, triethanolamine lauryl sulfate, and ammonium lauryl sulfate; polyoxyethylene alkyl sulfates such as sodium laureth sulfate and triethanolamine laureth sulfate; acyl N-methyl amino acid salts such as sodium cocoyl methyl taurate, potassium cocoyl methyl taurate, sodium lauroyl methyl taurate, sodium myristoyl methyl taurate, sodium lauroyl methylalaninate, sodium lauroyl sarcosinate, triethanolamine lauroyl sarcosinate, and sodium lauroyl glutamate methylalaninate; acylamino acid salts such as sodium cocoyl glutamate, triethanolamine cocoyl glutamate, sodium lauroyl glutamate, sodium myristoyl glutamate, sodium stearoyl glutamate, ditriethanolamine palmitoyl aspartate, and triethanolamine cocoyl alaninate; polyoxyethylene alkyl ether acetates such as sodium laureth acetate; succinic acid ester salts such as sodium lauroyl monoethanolamide succinate; fatty acid alkanolamide ether carboxylates; acyl lactates; polyoxyethylene fatty amine sulfates; fatty acid alkanolamide sulfates; fatty acid glyceride sulfates such as sodium glycerin hydrogenated coconut fatty acid sulfate; alkylbenzene polyoxyethylene sulfates; olefin sulfonates such as sodium α-olefin sulfonate; alkyl sulfosuccinates such as disodium lauryl sulfosuccinate and sodium dioctyl sulfosuccinate; alkyl ether sulfosuccinates such as disodium laureth sulfosuccinate, sodium monolauroyl monoethanolamide polyoxyethylene sulfosuccinate, and sodium lauryl polypropylene glycol sulfosuccinate; alkylbenzene sulfonates such as sodium tetradecylbenzene sulfonate and triethanolamine tetradecylbenzene sulfonate; alkyl naphthalene sulfonates; alkane sulfonates; α-sulfofatty acid methyl ester salts; acyl isethionates; alkyl glycidyl ether sulfonates; alkyl sulfoacetates; alkyl ether phosphoric acid ester salts such as sodium laureth phosphate, sodium dilaureth phosphate, sodium trilaureth phosphate, and sodium monooreth phosphate; alkyl phosphoric acid ester salts such as potassium lauryl phosphate; sodium caseinate; alkyl aryl ether phosphates; fatty acid amide ether phosphates; phospholipids such as phosphatidylglycerol, phosphatidylinositol, and phosphatidic acid; and silicone anionic surfactants such as carboxylic acid-modified silicones, phosphoric acid-modified silicones, and sulfuric acid-modified silicones.

Preferable examples of the nonionic surfactants include polyoxyethylene alkyl ethers with various numbers of polyoxyethylenes addition such as laureths (polyoxyethylene lauryl ethers), ceteths (polyoxyethylene cetyl ethers), steareths (polyoxyethylene stearyl ethers), beheneths (polyoxyethylene behenyl ethers), isosteareths (polyoxyethylene isostearyl ethers), and octyldodeceths (polyoxyethylene octyldodecyl ethers); polyoxyethylene alkyl phenyl ethers; castor oil derivatives and hydrogenated castor oil derivatives such as polyoxyethylene hydrogenated castor oil, polyoxyethylene castor oil, polyoxyethylene hydrogenated castor oil monoisostearate, polyoxyethylene hydrogenated castor oil triisostearate, polyoxyethylene hydrogenated castor oil monopyroglutamate monoisostearate diester, and polyoxyethylene hydrogenated castor oil maleate; polyoxyethylene phytosterol; polyoxyethylene cholesterol; polyoxyethylene cholestanol; polyoxyethylene lanolin; polyoxyethylene reduced lanolin; polyoxyethylene-polyoxypropylene alkyl ethers such as polyoxyethylene-polyoxypropylene cetyl ether, polyoxyethylene-polyoxypropylene 2-decyltetradecyl ether, polyoxyethylene-polyoxypropylene monobutyl ether, polyoxyethylene-polyoxypropylene hydrogenated lanolin, and polyoxyethylene-polyoxypropylene glycerin ether; polyoxyethylene-polyoxypropylene glycol; (poly)glycerin polyoxypropylene glycols such as PPG-9 diglyceryl; glycerin fatty acid partial esters such as glyceryl stearate, glyceryl isostearate, glyceryl palmitate, glyceryl myristate, glyceryl oleate, glyceryl cocoate, glycerin mono-cottonseed oil fatty acid, glycerin monoerucate, glycerin sesquioleate, glycerin α,α'-oleate pyroglutamate, and glycerin monostearate malate; polyglycerin fatty acid esters such as polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, polyglyceryl-6 distearate, polyglyceryl-10 distearate, polyglyceryl-2 tristearate, polyglyceryl-10 decastearate, polyglyceryl-2 isostearate, polyglyceryl-3 isostearate, polyglyceryl-4 isostearate, polyglyceryl-5 isostearate, polyglyceryl-6 isostearate, polyglyceryl-8 isostearate, polyglyceryl-10 isostearate, polyglyceryl-2 diisostearate (diglyceryl diisostearate), polyglyceryl-3 diisostearate, polyglyceryl-10 diisostearate, polyglyceryl-2 triisostearate, polyglyceryl-2 tetraisostearate, polyglyceryl-10 decaisostearate, polyglyceryl-2 oleate, polyglyceryl-3 oleate, polyglyceryl-4 oleate, polyglyceryl-5 oleate, polyglyceryl-6 oleate, polyglyceryl-8 oleate, polyglyceryl-10 oleate, polyglyceryl-6 dioleate, polyglyceryl-2 trioleate, and polyglyceryl-10 decaoleate; ethylene glycol mono-fatty acid esters such as ethylene glycol monostearate; propylene glycol mono-fatty acid esters such as propylene glycol monostearate; pentaerythritol fatty acid partial esters; sorbitol fatty acid partial esters; maltitol fatty acid partial esters; maltitol ether; sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, sorbitan penta-2-ethylhexylate diglycerol, and sorbitan tetra-2-ethylhexylate diglycerol; sugar derivative partial esters such as sucrose fatty acid esters, methyl glucoside fatty acid esters, and trehalose undecylenoate; alkyl glucosides such as caprylyl glucoside; alkyl polyglycosides; lanolin alcohol; reduced lanolin; polyoxyethylene fatty acid monoesters and polyoxyethylene fatty acid diesters such as polyoxyethylene distearate, polyethylene glycol diisostearate, polyoxyethylene monooleate, and polyoxyethylene dioleate; polyoxyethylene-propylene glycol fatty acid esters; polyoxyethylene glycerin fatty acid esters including polyoxyethylene glycerin monostearate, polyoxyethylene glycerin monoisostearate, and polyoxyethylene glycerin triisostearate; polyoxyethylene sorbitan fatty acid esters such as polyoxyethylene sorbitan monooleate, polyoxyethylene sorbitan monostearate, polyoxyethylene sorbitan monooleate, and polyoxyethylene sorbitan tetraoleate; polyoxyethylene sorbitol fatty acid esters such as polyoxyethylene sorbitol monolaurate, polyoxyethylene sorbitol monooleate, polyoxyethylene sorbitol pentaoleate, and polyoxyethylene sorbitol monostearate; polyoxyethylene methyl glucoside fatty acid esters; polyoxyethylene alkyl ether fatty acid esters; polyoxyethylene-modified animal and vegetable oils/fats such as polyoxyethylene sorbitol beeswax; alkyl glyceryl ethers such as isostearyl glyceryl ether, chimyl alcohol, selachyl alcohol, and batyl alcohol; polyhydric alcohol alkyl ethers; polyoxyethylene alkylamines; tetrapolyoxyethylene/tetrapolyoxypropylene-ethylenediamine condensates; natural surfactants such as saponins and sophorolipid; polyoxyethylene fatty acid amides; fatty acid alkanolamides such as coconut fatty acid monoethanolamide (cocamide MEA), coconut fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (palmitamide MEA), palmitic acid diethanolamide (palmitamide DEA), and coconut fatty acid methylethanolamide (cocamide methyl MEA); alkyl dimethylamine oxides such as lauramine oxide, cocamine oxide, stearamine oxide, and behenamine oxide; alkyl ethoxy dimethylamine oxides; polyoxyethylene alkyl mercaptans; and silicone nonionic surfactants such as polyether-modified silicones including dimethicone copolyols, polysiloxane-oxyalkylene copolymers, polyglycerin-modified silicones, and sugar-modified silicones.

Preferable examples of the cationic surfactants include alkyl trimethylammonium chlorides such as behentrimonium chloride, steartrimonium chloride, cetrimonium chloride, and lauryltrimonium chloride; alkyl trimethylammonium bromides such as stearyltrimonium bromide; dialkyl dimethylammonium chlorides such as distearyldimonium chloride and dicocodimonium chloride; fatty acid amide amines such as stearamide propyldimethylamine and stearamide ethyldiethylamine, and salts thereof; alkyl ether amines such as stearoxypropyldimethylamine, and salts thereof; quaternary salts thereof; fatty acid amide quaternary ammonium salts such as branched long-chain fatty acid (12 to 31)

aminopropylethyldimethylammonium ethyl sulfates and lanolin fatty acid aminopropylethyldimethylammonium ethyl sulfate; polyoxyethylene alkylamines, and salts and quaternary salts thereof; alkylamine salts; fatty acid amide guanidium salts; alkyl ether ammonium salts; alkyl trialkylene glycol ammonium salts; benzalkonium salts; benzethonium salts; pyridinium salts such as cetylpyridinium chloride; imidazolinium salts; alkyl isoquinolinium salts; dialkyl morpholinium salts; polyamine fatty acid derivatives; and silicone cationic surfactants such as amino-modified silicones including aminopropyl dimethicone and amodimethicone, cation-modified silicones, cation-modified and polyether-modified silicones, and amino-modified and polyether-modified silicones.

Preferable examples of the amphoteric surfactants include N-alkyl-N,N-dimethylamino acid betaines such as lauryl betaine (lauryl dimethylaminoacetic acid betaine); fatty acid amide alkyl-N,N-dimethylamino acid betaines such as cocamide propyl betaine and lauramide propyl betaine; imidazoline-type betaines such as sodium cocoamphoacetate and sodium lauroamphoacetate; alkyl sulfobetaines such as alkyl dimethyltaurines; sulfuric acid-type betaines such as alkyl dimethylamino ethanol sulfuric acid esters; phosphoric acid-type betaines such as alkyl dimethylamino ethanol phosphoric acid esters; phospholipids such as phosphatidylcholine, phosphatidylethanolamine, phosphatidylserine, sphingophospholipids including sphingomyelin, lysolecithin, hydrogenated soy phospholipid, partially hydrogenated soy phospholipid, hydrogenated egg-yolk phospholipid, partially hydrogenated egg-yolk phospholipid, and hydroxylated lecithin; and silicone amphoteric surfactants.

Preferable examples of the polymer surfactants include polyvinyl alcohol, sodium alginate, starch derivatives, tragacanth gum, and acrylic acid-alkyl methacrylate copolymers; and various silicone surfactants.

Preferable examples of the polymers, the thickeners, and the gelators include guar gum, locust bean gum, quince seed, carrageenan, galactan, gum arabic, tara gum, tamarind, furcellaran, karaya gum, *Abelmoschus manihot*, cara gum, tragacanth gum, pectin, pectic acid and salts thereof including a sodium salt thereof, alginic acid and salts thereof including a sodium salt thereof, and mannan; starches such as rice starch, corn starch, potato starch, and wheat starch; xanthan gum, dextran, succinoglucan, curdlan, hyaluronic acid and salts thereof, xanthan gum, pullulan, gellan gum, chitin, chitosan, agar, brown algae extract, chondroitin sulfate, casein, collagen, gelatin, and albumin; cellulose and derivatives thereof such as methylcellulose, ethylcellulose, hydroxyethylcellulose, hydroxypropylcellulose, hydroxypropyl methylcellulose, carboxymethylcellulose and salts thereof including sodium thereof, methylhydroxypropylcellulose, sodium cellulose sulfate, dialkyl dimethylammonium sulfate cellulose, crystalline cellulose, and cellulose powder; starch derivatives such as soluble starch, starch polymers including carboxymethyl starch, methylhydroxypropyl starch, and methyl starch, starch hydroxypropyltrimonium chloride, and aluminum corn starch octenylsuccinate; alginic acid derivatives such as sodium alginate and propylene glycol alginic acid ester; polyvinylpyrrolidone (PVP), polyvinyl alcohol (PVA), vinylpyrrolidone-vinyl alcohol copolymers, and polyvinyl methyl ether; polyethylene glycol, polypropylene glycol, and polyoxyethylene-polyoxypropylene copolymers; amphoteric methacrylic acid ester copolymers such as (methacryloyloxyethylcarboxy betaine/alkyl methacrylate) copolymers and (acrylate/stearyl acrylate/ethylamine oxide methacrylate) copolymers; (dimethicone/vinyl dimethicone) crosspolymer, (alkyl acrylate/diacetone acrylamide) copolymer, and (alkyl acrylate/diacetone acrylamide) copolymer AMP; partially saponified polyvinyl acetate and maleic acid copolymers; vinylpyrrolidone-dialkyl aminoalkyl methacrylate copolymers; acrylic resin alkanolamines; polyesters and water-dispersable polyesters; polyacrylamides; polyacrylic acid ester copolymers such as ethyl polyacrylate, carboxyvinyl polymers, polyacrylic acid and salts thereof including a sodium salt thereof, acrylic acid-methacrylic acid ester copolymers; acrylic acid-alkyl methacrylate copolymers; cationized celluloses such as polyquarternium-10, diallyldimethylammonium chloride-acrylamide copolymers such as polyquaternium-7, acrylic acid-diallyldimethylammonium chloride copolymers such as polyquaternium-22, acrylic acid-diallyldimethylammonium chloride-acrylamide copolymers such as polyquaternium-39, acrylic acid-cationized methacrylic acid ester copolymers, acrylic acid-cationized methacrylic acid amide copolymers, acrylic acid-methyl acrylate-methacrylamide propyltrimethylammonium chloride copolymers such as polyquaternium-47, and methacryloyl chloride choline ester polymers; cationized polysaccharides such as cationized oligosaccharides, cationized dextran, and guar hydroxypropyltrimonium chloride; polyethyleneimines; cationic polymers; polymers of 2-methacryloyloxyethylphosphorylcholine such as polyquarternium-51, and copolymers thereof with butyl methacrylate copolymer and the like; polymer emulsions such as acrylic resin emulsions, ethyl polyacrylate emulsions, polyacrylic alkyl ester emulsions, polyvinyl acetate resin emulsions, natural rubber latex, and synthetic latex; nitrocellulose; polyurethanes and various copolymers thereof; various silicones; various silicone copolymers such as acrylic-silicone graft copolymers; various fluoropolymers; 12-hydroxystearic acid and salts thereof; dextrin fatty acid esters such as dextrin palmitate and dextrin myristate; and silicic anhydride, fumed silica (silicic anhydride ultra-fine particles), magnesium aluminum silicate, magnesium sodium silicate, metal soaps, metal dialkyl phosphates, bentonite, hectorite, organo-modified clay mineral, sucrose fatty acid esters, and fructooligosaccharide fatty acid esters. Among them, cellulose and derivatives thereof, alginic acid and salts thereof, polyvinyl alcohol, hyaluronic acid and salts thereof, and collagen are preferable.

Preferable examples of the solvents and the propellants include lower alcohols such as ethanol, 2-propanol (isopropyl alcohol), butanol, and isobutyl alcohol; glycols such as propylene glycol, 1,3-butylene glycol, diethylene glycol, dipropylene glycol, and isopentyldiol; glycol ethers such as diethylene glycol monoethyl ether (ethoxydiglycol), ethylene glycol monoethyl ether, ethylene glycol monobutyl ether, triethylene glycol monoethyl ether, diethylene glycol diethyl ether, diethylene glycol dibutyl ether, propylene glycol monoethyl ether, and dipropylene glycol monoethyl ether; glycol ether esters such as ethylene glycol monoethyl ether acetate, diethylene glycol monoethyl ether acetate, and propylene glycol monoethyl ether acetate; glycol esters such as diethoxyethyl succinate and ethylene glycol disuccinate; benzyl alcohol, benzyloxyethanol, propylene carbonate, dialkyl carbonate, acetone, ethyl acetate, and N-methylpyrrolidone; toluene; fluorocarbon and next-generation fron; and propellants such as LPG, dimethyl ether, and carbon dioxide gas.

Preferable examples of the antioxidants include tocopherol (vitamin E) and tocopherol derivatives such as tocopherol acetate; BHT and BHA; gallic acid derivatives such as propyl gallate; vitamin C (ascorbic acid) and/or derivatives thereof; erythorbic acid and derivatives thereof; sulfites such as sodium sulfite; hydrogen sulfites such as sodium hydrogen sulfite; thiosulfates such as sodium thiosulfate; hydrogen metasulfites; thiotaurine and hypotaurine; and thioglycerol, thiourea, thioglycolic acid, and cysteine hydrochloride.

Preferable examples of the reducing agents include thioglycolic acid, cysteine, and cysteamine.

Preferable examples of the oxidizing agents include a hydrogen peroxide solution, ammonium persulfate, sodium bromate, and percarbonic acid.

Preferable examples of the preservatives, the antimicrobial agents, and the antiseptics include hydroxybenzoic acids and salts and esters thereof such as methylparaben, ethylparaben, propylparaben, and butylparaben; salicylic acid; sodium benzoate; phenoxyethanol; isothiazolinone derivatives such as methylchloroisothiazolinone and methylisothiazolinone; imidazolinium urea; dehydroacetic acid and salts thereof; phenols; halogenated bisphenols such as triclosan, acid amides, and quaternary ammonium salts; trichlorocarbanilide, zinc pyrithione, benzalkonium chloride, benzethonium chloride, sorbic acid, chlorhexidine, chlorhexidine gluconate, halocarban, hexachlorophene, and hinokitiol; phenol and other phenols such as isopropylphenol, cresol, thymol, p-chlorophenol, phenylphenol, and sodium phenylphenolate; and phenylethyl alcohol, photosensitive dyes, antimicrobial zeolite, and a silver ion.

Preferable examples of the chelating agents include edetates (ethylenediamine tetraacetates) such as EDTA, EDTA-2Na, EDTA-3Na, and EDTA-4Na; hydroxyethylethylenediaminetriacetates such as HEDTA-3Na; pentetates (diethylenetriaminepentaacetate); phytic acid; phosphonic acids such as etidronic acid, and salts thereof including sodium salts thereof; polyamino acids such as polyaspartic acid and polyglutamic acid; sodium polyphosphate, sodium metaphosphate, and phosphoric acid; and sodium citrate, citric acid, alanine, dihydroxyethylglycine, gluconic acid, ascorbic acid, succinic acid, and tartaric acid.

Preferable examples of the pH-adjusters, acids, and alkalis include citric acid, sodium citrate, lactic acid, sodium lactate, potassium lactate, glycolic acid, succinic acid, acetic acid, sodium acetate, malic acid, tartaric acid, fumaric acid, phosphoric acid, hydrochloric acid, sulfuric acid, monoethanolamine, diethanolamine, triethanolamine, isopropanolamine, triisopropanolamine, 2-amino-2-methyl-1,3-propanediol, 2-amino-2-hydroxymethyl-1,3-propanediol, arginine, sodium hydroxide, potassium hydroxide, an aqueous ammonia solution, guanidine carbonate, and ammonium carbonate.

Preferable examples of the powders include inorganic powders of various sizes and shapes such as mica, talc, kaolin, sericite, montmorillonite, kaolinite, mica, muscovite, phlogopite, synthetic mica, lepidolite, biotite, vermiculite, magnesium carbonate, calcium carbonate, aluminum silicate, barium silicate, calcium silicate, magnesium silicate, strontium silicate, metal tungstates, magnesium, zeolite, barium sulfate, calcined calcium sulfate, calcium phosphate, fluorapatite, hydroxyapatite, ceramic powder, bentonite, smectite, clay, mud, metal soaps (zinc myristate, calcium palmitate, and aluminum stearate, for example), calcium carbonate, red iron oxide, yellow iron oxide, black iron oxide, ultramarine, prussian blue, carbon black, titanium oxide, titanium oxide fine particles and titanium oxide ultrafine particles, zinc oxide, zinc oxide fine particles and zinc oxide ultrafine particles, alumina, silica, fumed silica (silicic anhydride ultrafine particles), titanated mica, fish scale guanine, boron nitride, photochromic pigments, synthetic fluorophlogopite, fine-particle composite powders, gold, and aluminum, and inorganic powders that are treated with a silicone such as hydrogen silicone and cyclic hydrogen silicone or are otherwise treated with various surface-treating agents such as silane coupling agents and titanium coupling agents to hydrophobize or hydrophilize these inorganic powders; and organic powders, surface-treated organic powders, and organic-inorganic composite powders of various sizes and shapes such as starch, cellulose, nylon powder, polyethylene powder, polymethyl methacrylate powder, polystyrene powder, styrene-acrylate copolymer resin powder, polyester powder, benzoguanamine resin powder, polyethylene terephthalate/polymethyl methacrylate-laminated powder, polyethylene terephthalate/aluminum/epoxy-laminated powder, urethane powder, silicone powder, and Teflon (registered trademark) powder.

Preferable examples of the inorganic salts include sodium chloride-containing salts such as common salt, regular salt, rock salt, sea salt, and natural salt; potassium chloride, aluminum chloride, calcium chloride, magnesium chloride, bittern, zinc chloride, and ammonium chloride; sodium sulfate, aluminum sulfate, aluminum potassium sulfate (alum), aluminum ammonium sulfate, barium sulfate, calcium sulfate, potassium sulfate, magnesium sulfate, zinc sulfate, iron sulfate, and copper sulfate; and sodium phosphates such as mono-, di-, and trisodium phosphates, potassium phosphates, calcium phosphates, and magnesium phosphates.

Preferable examples of the ultraviolet absorbers include benzoate-based ultraviolet absorbers such as p-aminobenzoic acid, p-aminobenzoic acid monoglycerin ester, N,N-dipropoxy p-aminobenzoic acid ethyl ester, N,N-diethoxy p-aminobenzoic acid ethyl ester, N,N-dimethyl p-aminobenzoic acid ethyl ester, N,N-dimethyl p-aminobenzoic acid butyl ester, and N,N-dimethyl p-aminobenzoic acid ethyl ester; anthranilate-based ultraviolet absorbers such as homomenthyl-N-acetylanthranilate; salicylate-based ultraviolet absorbers such as salicylic acid and a sodium salt thereof, amyl salicylate, menthyl salicylate, homomenthyl salicylate, octyl salicylate, phenyl salicylate, benzyl salicylate, and p-isopropanolphenyl salicylate; cinnamate-based ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethylhexyl p-methoxy cinnamate (octyl p-methoxy cinnamate), 2-ethoxyethyl-p-methoxy cinnamate (cinoxate), cyclohexyl-p-methoxy cinnamate, ethyl-α-cyano-β-phenyl cinnamate, 2-ethylhexyl α-cyano-β-phenyl cinnamate (octocrylene), glyceryl mono-2-ethylhexanoyl-di-p-methoxy cinnamate, and ferulic acid and derivatives thereof; benzophenone-based ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone (oxybenzone-3), 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor and 3-benzylidene-d,l-camphor; 2-phenyl-5-methylbenzoxazole; 2,2'-hydroxy-5-methylphenylbenzotriazole; 2-(2'-hydroxy-5'-tert-octylphenyl)benzotriazole; 2-(2'-hydroxy-5'-methylphenyl)benzotriazole; dibenzalazines; dianisoylmethane; 5-(3,3-dimethyl-2-norbornylidene)-3-pentan-2-one; dibenzoylmethane derivatives such as 4-tert-butylmethoxydibenzoylmethane; octyl triazone; urocanic acid, and urocanic acid derivatives such as ethyl urocanate; and 2-(2'-hydroxy-5'-methylphenyl)benzotriazole, 1-(3,4- dimethoxyphenyl)-4,4-dimethyl-1,3-pentanedione, hydantoin derivatives such as 2-ethylhexyl dimethoxybenzylidene dioxoimidazolidine propionate, phenylbenzimidazole sulfonic acid, terephthalylidene dicamphor sulfonic acid, drometrizole trisiloxane, methyl antlaranilate, rutin and derivatives thereof, and orizanol and derivatives thereof.

Preferable examples of the skin-brightening agents include hydroquinone glycosides such as arbutin and α-arbutin, and esters thereof; ascorbic acid and ascorbic acid derivatives such as ascorbyl phosphate salts including sodium ascorbyl phosphate and magnesium ascorbyl phosphate, ascorbyl fatty acid esters including ascorbyl tetraisopalmitate, ascorbic acid alkyl ethers including ascorbic acid ethyl ether, ascorbic acid glucosides including ascorbic acid 2-glucoside and fatty acid esters thereof, ascorbyl sulfate, and tocopheryl ascorbyl phosphate; and kojic acid, ellagic acid, tranexamic acid and derivatives thereof, ferulic acid and derivatives thereof, placenta extract, glutathione, orizanol, butyl resorcinol, and plant extracts such as oil-soluble *Chamomilla recutita* extract, oil-soluble licorice extract, *Tamarix chinensis* extract, and *Saxifraga sarmentosa* extract.

Preferable examples of the vitamins and derivatives thereof include the vitamin A group such as retinol, retinol acetate, and retinol palmitate; the vitamin B group such as thiamine hydrochloride, thiamine sulfate, riboflavin, riboflavin acetate, pyridoxine hydrochloride, pyridoxine dioctanoate, pyridoxine dipalmitate, flavin adenine dinucleotide, cyanocobalamine, folic acids, nicotinic acids such as nicotinamide and benzyl nicotinate, and cholines; the vitamin C group such as ascorbic acid and salts thereof including sodium thereof; vitamin D; the vitamin E group such as α-, β-, γ-, and δ-tocopherols; other vitamins such as pantothenic acid and biotin; ascorbic acid derivatives such as ascorbyl phosphate salts including ascorbyl phosphate sodium salt and ascorbyl phosphate magnesium salt, ascorbyl fatty acid esters including ascorbyl tetraisopalmitate, ascorbyl stearate, ascorbyl palmitate, and ascorbyl dipalmitate, ascorbic acid alkyl ethers including ascorbic acid ethyl ether, ascorbic acid glucosides including ascorbic acid 2-glucoside and fatty acid esters thereof, and tocopheryl ascorbyl phosphate; and vitamin derivatives such as tocopherol derivatives including tocopherol nicotinate, tocopherol acetate, tocopherol linoleate, tocopherol ferulate, and tocopherol phosphate, tocotrienol, and other various vitamin derivatives.

Preferable examples of the hair growth-promoting agents, the blood circulation-promoters, and the stimulating agents include plant extracts and tinctures such as Swertia herb extract, *Capsicum frutescens* tincture, ginger tincture, ginger extract, and cantharides tincture; and capsaicin, nonylic acid vanillylamide, zingerone, ichthammol, tannic acid, borneol, cyclandelate, cinnarizine, tolazoline, acetylcholine, verapamil, cepharanthine, γ-orizanol, vitamin E and derivatives thereof including tocopherol nicotinate and tocopherol acetate, γ-orizanol, nicotinic acid and derivatives thereof including nicotinamide, benzyl nicotinate, inositol hexanicotinate, and nicotinic alcohol, allantoin, Kankoso 301, Kankoso 401, carpronium chloride, pentadecanoic acid monoglyceride, flavanonol derivatives, stigmasterol and stigmastanol and glycosides thereof, and minoxidil.

Preferable examples of the hormones include estradiol, estrone, ethynylestradiol, cortisone, hydrocortisone, and prednisone. Preferable examples of other substances with drug efficacy such as the anti-wrinkle agents, the anti-aging agents, the tightening agents, the cool-feeling agents, the warm-feeling agents, the wound-healing promoters, the abirritants, the analgesics, and the cell activators include retinols, retinoic acids, and tocopheryl retinoate; lactic acid, glycolic acid, gluconic acid, fruit acid, and salicylic acid and derivatives thereof including glycosides thereof and esters thereof, and α- and β-hydroxy acids and derivatives thereof such as hydroxycapric acid, long-chain α-hydroxy fatty acids, long-chain α-hydroxy fatty acid cholesteryl esters; γ-aminobutyric acid and γ-amino-β-hydroxybutyric acid; carnitine; carnosine; creatine; ceramides and sphingosines; caffeine, xanthine, and the like and derivatives thereof; antioxidizing agents and active oxygen scavengers such as coenzyme Q10, carotin, lycopene, astaxanthin, lutein, α-lipoic acid, colloidal platinum nanoparticles, and fullerenes; catechins; flavones such as quercetin; isoflavones; gallic acid and sugar ester derivatives thereof; polyphenols such as tannin, sesamin, proanthocyanidin, chlorogenic acid, and apple polyphenol; rutin and derivatives thereof including glycosides thereof; hesperidin and derivatives thereof including glycosides thereof; lignan glycoside; licorice extract-related substances such as glabridin, glabrene, liquiritin, and isoliquiritin; lactoferrin; shogaol and gingerol; perfume substances such as menthol and cedrol, and derivatives thereof; capsaicin, vanillin, and the like and derivatives thereof; insect repellents such as diethyltoluamide; and complexes of physiologically active substances and cyclodextrins.

Preferable examples of the plant, animal, and microbial extracts include extracts such as iris extract, *Angelica keiskei* extract, *Thujopsis dolabrata* extract, asparagus extract, avocado extract, *Hydrangea serrata* extract, almond extract, *Althaea officinalis* extract, *Arnica montana* extract, aloe extract, apricot extract, apricot kernel extract, *Gingko biloba* extract, *Artemisia capillaris* flower extract, fennel seed extract, turmeric root extract, oolong tea extract, *Arctostaphylos uva-ursi* leaf extract, *Rosa multiflora* fruit extract, *Echinacea angustifolia* leaf extract, *Isodonis japonicus* extract, *Scutellaria baicalensis* extract, *Phellodendron amurense* bark extract, *Coptis japonica* root extract, *Hordeum vulgare* extract, *Panax ginseng* extract, *Hypericum perforatum* extract, *Lamium album* extract, *Ononis spinosa* extract, *Nasturtium officinale* extract, orange extract, dried sea water residues, seaweed extract, Persimmon leaf extract, *Pyracantha fortuneana* extract, hydrolyzed elastin, hydrolyzed wheat powder, hydrolyzed silk, *Pueraria lobata* root extract, *Chamomilla recutita* extract, oil-soluble *Chamomilla recutita* extract, *Daucus carota sativa* extract, *Artemisia capillaris* extract, *Avena fatua* extract, carcade extract, licorice extract, oil-soluble licorice extract, kiwi fruit extract, kiou extract, *Auricularia auricula-judae* extract, *Cinchona succirubra* extract, cucumber extract, *Paulownia tomentosa* leaf extract, guanosine, guava extract, *Sophora angustifolia* extract, *Gardenia florida* extract, *Sasa veitchii* extract, *Sophora angustifolia* extract, walnut extract, chestnut extract, grapefruit extract, *Clematis vitalba* extract, black rice extract, black sugar extract, black vinegar, *Chlorella vulgaris* extract, *Morus alba* extract, *Gentiana lutea* extract, *Geranium thunbergii* extract, black tea extract, yeast extract, *magnolia* bark extract, coffee seed extract, *Arctium lappa* root extract, rice extract, fermented rice extract, fermented rice bran extract, rice germ oil, *Symphytum officinale* extract, collagen, *Vaccinium vitis-idaea* extract, *Asarum sieboldi* extract, *Bupleurum falcatum* extract, umbilical extract, saffron extract, *salvia* extract, *Saponaria officinalis* extract, *sasa* extract, *Crataegus cuneata* fruit extract, *Bombyx mori excrementum* extract, *Zanthoxylum piperitum* extract, *Corthellus shiitake* extract, *Rehmannia glutinosa* extract, *Lithospermum erythrorhizon* root extract, *Perilla ocymoides* extract, *Tilia cordata* extract, *Spiraea*

*ulmaria* extract, jatoba extract, *Paeonia albiflora* extract, ginger extract, *Acorus calamus* root extract, *Betula platyphylla Japonica* extract, *Tremella fuciformis* extract, *Equisetum arvense* extract, stevia fermentation product, *Tamarix chinensis* extract, *Hedera helix* extract, *Crataegus oxyacantha* extract, *Sambucus nigra* extract, *Achillea millefolium* extract, *Mentha piperita* extract, sage extract, *Malva sylvestris* extract, *Cnidium officinale* extract, Swertia herb extract, Moms alba root extract, Rheum extract, soybean extract, *Zizyphus jujuba* extract, thyme extract, dandelion extract, lichen extract, *Camellia sinensis* leaf extract, clove extract, *Imperata cylindrica* extract, *Citrus unshiu* peel extract, tea tree oil, *Rubus suavissimus* extract, *Capsicum frutescens* extract, *Angelica acutiloba* extract, *Calendula officinalis* extract, *Prunus persica* kernel extract, *Citrus aurantium amara* peel extract, *Houttuynia cordata* extract, tomato extract, natto extract, carrot extract, garlic extract, *Rosa canina* extract, hibiscus extract, *Ophiopogon japonicus* root extract, *Nelumbo nucifera* extract, parsley extract, birch extract, honey, *Hamamelis virginiana* extract, *Parietaria officinalis* extract, *Isodonis japonicus* extract, bisabolol, *Chamaecyparis obtusa* extract, Bifidobacterium extract, *Eriobotrya japonica* extract, *Tussilago farfara* extract, *Petasites japonicus* flower stalk extract, *Poria cocos sclerotium* extract, *Ruscus aculeatus* extract, grape extract, grape seed extract, propolis, *Luffa cylindrica* extract, safflower extract, peppermint extract, *Tilia miqueliana* extract, *Paeonia suffruticosa* root extract, hops extract, *Rosa rugosa* flower extract, *Pinus sylvestris* cone extract, horse chestnut extract, *Lysichiton camtschatcense* extract, *Sapindus mukurossi* peel extract, *Melissa officinalis* extract, *Nemacystus decipiens* extract, peach extract, *Centaurea cyanus* extract, *Eucalyptus globulus* extract, Saxifraga *sarmentosa* extract, *Citrus junos* extract, lily extract, *Coix lacryma-jobi* seed extract, *Artemisia princeps* extract, lavender extract, green tea extract, egg shell membrane extract, apple extract, rooibos tea extract, *Ganoderma lucidum* extract, lettuce extract, lemon extract, forsythia extract, *Astragalus sinicus* extract, rose extract, rosemary extract, *Anthemis nobilis* extract, royal jelly extract, and *Sanguisorba officinalis* root extract.

Examples of the antipruritics include diphenhydramine hydrochloride, chlorpheniramine maleate, camphor, and substance P inhibitors.

Examples of the keratin-exfoliating/dissolving agents include salicylic acid, sulfur, resorcin, selenium sulfide, and pyridoxine.

Examples of the antiperspirants include aluminum chlorohydrate, aluminum chloride, zinc oxide, and zinc p-phenolsulfonate.

Examples of the refrigerants include menthol and methyl salicylate.

Examples of the styptics include citric acid, tartaric acid, lactic acid, aluminum potassium sulfate, and tannic acid.

Examples of the enzymes include superoxide dismutases, catalases, lysozyme chloride, lipases, papain, pancreatin, and proteases.

Preferable examples of the nucleic acids include ribonucleic acid and salts thereof, deoxyribonucleic acid and salts thereof, and adenosine triphosphate disodium.

Preferable examples of the perfumes include synthetic perfumes and natural perfumes such as acetyl cedrene, amylcinnamaldehyde, allylamyl glycolate, β-ionone, Iso E Super, isobutylquinoline, iris oil, irone, indole, ylang-ylang oil, undecanal, undecenal, γ-undecalactone, estragole, eugenol, oakmoss, opoponax resinoid, orange oil, eugenol, aurantiol, galaxolide, carvacrol, L-carvone, camphor, canon, carrot seed oil, clove oil, methyl cinnamate, geraniol, geranyl nitrile, isobornyl acetate, geranyl acetate, dimethylbenzylcarbinyl acetate, styralyl acetate, cedryl acetate, terpinyl acetate, p-t-butylcyclohexyl acetate, vetiveryl acetate, benzyl acetate, linalyl acetate, isopentyl salicylate, benzyl salicylate, sandalwood oil, santalol, cyclamen aldehyde, cyclopentadecanolide, methyl dihydrojasmonate, dihydromyrcenol, jasmine absolute, jasmin lactone, cis-jasmone, citral, citronellol, citronellal, cinnamon bark oil, 1,8-cineole, cinnamaldehyde, styrax resinoid, cedarwood oil, cedrene, cedrol, celery seed oil, thyme oil, damascone, damascenone, thymol, tuberose absolute, decanal, decalactone, terpineol, γ-terpinen, triplal, nerol, nonanal, 2,6-nonadienol, nonalactone, patchouli alcohol, vanilla absolute, vanillin, basil oil, patchouli oil, hydroxycitronellal, α-pinene, piperitone, phenethyl alcohol, phenylacetaldehyde, petitgrain oil, hexylcinnamaldehyde, cis-3-hexenol, Peru balsam, vetiver oil, vetiverol, peppermint oil, pepper oil, heliotropin, bergamot oil, benzyl benzoate, borneol, mil resinoid, musk ketone, methyl nonyl acetaldehyde, γ-methyl ionone, menthol, L-menthol, L-menthone, *Eucalyptus globulus* oil, β-ionone, lime oil, lavender oil, D-limonene, linalool, lyral, lilial, lemon oil, rose absolute, rose oxide, rose oil, rosemary oil, and various essential oils, and various perfume blends.

Preferable examples of the coloring agents, the colorants, the dyes, and the pigments include Japanese cosmetic colors such as Brown No. 201, Black No. 401, Violet No. 201, Violet No. 401, Blue No. 1, Blue No. 2, Blue No. 201, Blue No. 202, Blue No. 203, Blue No. 204, Blue No. 205, Blue No. 403, Blue No. 404, Green No. 201, Green No. 202, Green No. 204, Green No. 205, Green No. 3, Green No. 401, Green No. 402, Red No. 102, Red No. 104-1, Red No. 105-1, Red No. 106, Red No. 2, Red No. 201, Red No. 202, Red No. 203, Red No. 204, Red No. 205, Red No. 206, Red No. 207, Red No. 208, Red No. 213, Red No. 214, Red No. 215, Red No. 218, Red No. 219, Red No. 220, Red No. 221, Red No. 223, Red No. 225, Red No. 226, Red No. 227, Red No. 228, Red No. 230-1, Red No. 230-2, Red No. 231, Red No. 232, Red No. 3, Red No. 401, Red No. 404, Red No. 405, Red No. 501, Red No. 502, Red No. 503, Red No. 504, Red No. 505, Red No. 506, Orange No. 201, Orange No. 203, Orange No. 204, Orange No. 205, Orange No. 206, Orange No. 207, Orange No. 401, Orange No. 402, Orange No. 403, Orange No. 404, Yellow No. 201, Yellow No. 202-1, Yellow No. 202-2, Yellow No. 203, Yellow No. 204, Yellow No. 205, Yellow No. 4, Yellow No. 401, Yellow No. 402, Yellow No. 403-1, Yellow No. 404, Yellow No. 405, Yellow No. 406, Yellow No. 407, and Yellow No. 5; other acid dyes such as Acid Red No. 14; basic dyes such as Arianor Sienna Brown, Arianor Madder Red, Arianor Steel Blue, and Arianor Straw Yellow; nitro dyes such as HC Yellow No. 2, HC Yellow No. 5, HC Red No. 3, 4-hydoxypropylamino-3-nitrophenol, N,N'-bis(2-hydroxyethyl)-2-nitro-p-phenylenediamine, HC Blue No. 2, and Basic Blue No. 26; disperse dyes; inorganic white pigments such as titanium dioxide and zinc oxide; inorganic red pigments such as iron oxide (red iron oxide) and iron titanate; inorganic brown pigments such as γ-iron oxide; inorganic yellow pigments such as yellow iron oxide and ochre; inorganic black pigments such as black iron oxide and low-order titanium oxide; inorganic violet pigments such as mango violet and cobalt violet; inorganic green pigments such as chromium oxide, chromium hydroxide, and cobalt titanium oxide; inorganic blue pigments such as ultramarine and prussian blue; pearl pigments such as titanium oxide-coated mica, titanium oxide-coated bismuth oxychloride, titanium oxide-coated talc, colored titanium oxide-coated mica, bismuth oxychloride, and fish scale guanine; metal powder pigments such as aluminum powder, copper powder, and gold; surface-treated inorganic and metallic powder pigments; organic pigments such as zirconium lake, barium lake, and aluminum lake; surface-treated organic pigments; natural coloring agents and natural dyes such as astaxanthin, anthraquinones including alizarin, anthocyanidine, β-carotin, carotenal, capsanthin, chalcone, carthamin, quercetin, crocin, chlorophyll, curcumin, cochineal, naphthoquinones including shikonin, bixin, flavones, betacyanin, henna, hemoglobin, lycopene, riboflavin, and rutin; oxidation dye intermediates and couplers such as p-phenylenediamine, toluene-2,5-diamine, o-, m-, and p-aminophenols, m-phenylenediamine, 5-amino-2-methyl phenol, resorcin, 1-naphthol, 2,6-diaminopyridine, and the like, and salts thereof; autoxidizable dyes such as indoline; and dihydroxyacetone.

Preferable examples of the antiphlogistics and the anti-inflammatory agents include glycyrrhizic acid and derivatives thereof, glycyrrhetinic acid derivatives, salicylic acid derivatives, hinokitiol, guaiazulene, allantoin, indomethacin, ketoprofen, ibuprofen, diclofenac, loxoprofen, celecoxib, infliximab, etanercept, zinc oxide, hydrocortisone acetate, prednisone, diphenhydramine hydrochloride, and chlorpheniramine maleate; and plant extracts such as peach leaf extract and *Artemisia princeps* leaf extract.

Preferable examples of the anti-asthmatic agents, the drugs for chronic obstructive pulmonary disease, the anti-allergic agents, and the immunomodulators include aminophylline, theophyllines, steroids (fluticasone, beclomethasone, and the like), leukotriene antagonists, thromboxane inhibitors, Intal, β2-agonists (formoterol, salmeterol, albuterol, tulobuterol, clenbuterol, epinephrine, and the like), tiotropium, ipratropium, dextromethorphan, dimemorfan, bromhexine, tranilast, ketotifen, azelastine, cetirizine, chlorpheniramine, mequitazine, tacrolimus, cyclosporin, sirolimus, methotrexate, cytokine modulators, interferon, omalizumab, and proteins and antibodies.

Preferable examples of the anti-infective agents and the antifungal agents include oseltamivir, zanamivir, and itraconazole. Other than these, known cosmetic ingredients, known pharmaceutical ingredients, known food ingredients, and the like such as ingredients described in The Japanese Standards of Cosmetic Ingredients, Japanese Cosmetic Ingredients Codex, Japanese Cosmetic Labeling Name list issued by Japan Cosmetic Industry Association, INCI dictionary (The International Cosmetic Ingredient Dictionary and Handbook), Japanese Standards of Quasi-drug Ingredients, Japanese Pharmacopoeia, Japanese Pharmaceutical Excipients, Japan's Specifications and Standards for Food Additives, and the like and ingredients described in Japanese and foreign patent publications and Patent Application Publications (including Japanese Translations of PCT International Applications and Domestic Re-Publications of PCT International Applications) categorized as International Patents Classification IPC of A61K7 and A61K8 can be included in a known combination and in a known formulation ratio or in a known formulation amount.

[Method of Producing Thickened Composition]

The thickened composition of the present invention comprises the lipid peptide compound containing at least one of the compound of Formula (1) to Formula (3) and a pharmaceutically usable salt thereof, the polyhydric alcohol, water, and the organic acid, and can be produced, with the use of a fatty acid, a surfactant, and other additives when desired, by mixing and stirring them while heating, followed by leaving the resultant mixture still standing to cool.

The thickened composition of the present invention is produced, for example, by the following steps.

a) a step of mixing the lipid peptide compound and the polyhydric alcohol and heating the resultant mixture to prepare a solution or a dispersion (premix phase)

b) a step of heating the solution or the dispersion (premix phase) at a temperature not lower than room temperature and lower than 100° C.

c) a step of mixing the polyhydric alcohol, water, and the organic acid and heating the resultant mixture to prepare a solution or a dispersion (aqueous phase)

d) a step of heating the solution or the dispersion (aqueous phase) at a temperature not lower than room temperature and lower than 100° C.

e) a step of mixing the premix phase thus heated and the aqueous phase thus heated, cooling the resultant mixture with stirring to a temperature lower than the temperatures in the heating steps, and then leaving the resultant mixture still standing to cool to form a thickened composition The fatty acid, the surfactant, and other additives may be added in the step a) of preparing the solution or the dispersion (premix phase), or in the step c) of preparing the solution or the dispersion (aqueous phase).

The amount of water is preferably not lower than 20% by mass and lower than 90% by mass relative to the total mass of the resulting thickened composition.

The amount of water is preferably not lower than 40% by mass and lower than 80% by mass relative to the total mass of the resulting solution or the resulting dispersion (aqueous phase).

The temperature in heating in the step b) and the step d) is preferably from 50° C. to 90° C. and more preferably from 60° C. to 90° C., and is 80° C., for example. The heating is preferably accompanied by stirring.

The time of heating with stirring in each step varies depending on the types of the lipid peptide compound, the polyhydric alcohol, the organic acid, and other components, as well as the amounts of them to be added. Usually, dissolution and dispersion can be completed in about 5 minutes to about 50 minutes.

After the step d), cooling is performed with stirring until the temperature of the liquid becomes lower than the temperatures in the steps b) and d) (the step (e)). The cooling temperature is from room temperature to about 80° C., from room temperature to about 60° C., or from room temperature to about 40° C., for example.

The present invention also relates to a feedstock premix for preparation of the thickened composition of the present invention, the feedstock premix comprising the polyhydric alcohol, water, and the lipid peptide-type compound containing at least one of the compound of Formula (1) to Formula (3) above and a pharmaceutically usable salt thereof. A preferable premix further comprises at least one fatty acid.

EXAMPLES

The present invention will be described in more detail by examples and test examples. The scope of the present invention, however, is not limited to these examples.

Synthesis Example 1: Synthesis of Lipid Peptide (N-Palmitoyl-Gly-His)

A lipid peptide used in this example as a gelator was synthesized by a method below.

14.2 g (91.6 mmol) of histidine, 30.0 g (91.6 mmol) of N-palmitoyl-Gly-methyl, and 300 g of toluene were added to a 500-mL four-necked flask, to which 35.3 g (183.2 mmol) of a 28% methanol solution of sodium methoxide as a base was added, and the resultant mixture was heated in an oil bath to 60° C. and was stirred for 1 hour. Subsequently, the resulting solution that was removed from the oil bath was left to cool to reach 25° C., was reprecipitated with 600 g of acetone, and was filtered. The resulting solid was dissolved in a mixed solution of 600 g of water and 750 g of methanol, to which 30.5 ml (183.2 mmol) of 6-N hydrochloric acid was added for neutralization to precipitate a solid, which was filtered. The resulting solid was then dissolved in a mixed solution of 120 g of tetrahydrofuran and 30 g of water at 60° C., to which 150 g of ethyl acetate was added, and the resulting solution was cooled from 60° C. to 30° C. Subsequently, the precipitated solid was filtrated. The resulting solid was dissolved in a solvent of 120 g of tetrahydrofuran and 60 g of acetonitrile and then heated to 60° C. The resulting solution was stirred for 1 hour and then cooled, followed by filtration. The resulting solid was washed with 120 g of water and filtrated, followed by drying under reduced pressure to obtain 26.9 g (yield: 65%) of a white crystal of a free form of N-palmitoyl-Gly-His.

Example 1 to Example 11

Preparation 1 of Ascorbic Acid Thickened Composition

Compositions 1 to 11 shown in Table 1 were prepared by the following procedure

Components of a premix phase were weighed according to the amounts thereof to be added shown in Table 1, into a sample tube No. 5 (manufactured by Maruemu Corporation). Components of an aqueous phase were also weighed according to the amounts thereof to be added shown in Table 1, into a 300-mL tall beaker. Then, the premix phase and the aqueous phase were heated to not lower than 70° C., respectively. Subsequently, the premix phase and the aqueous phase were mixed, followed by stifling to cool. Stirring was stopped when the temperature of the liquid reached 40° C., and, thus, a composition sample was prepared.

The viscosity of the sample thus prepared was measured with a viscometer (AND VIBRO VISCOMETER SU-1A). The value of the viscosity used was the one measured 1 minute after vibration was applied. The results are shown in Table 1. In Table 1, Pal-GH refers to the lipid peptide obtained in Synthesis Example 1 (free form of N-palmitoyl-Gly-His), and BG refers to 3-butylene glycol.

TABLE 1

Amounts of components to be added, in 100 g of ascorbic acid thickened composition (Example 1 to Example 11)

| Phase | Composition | 1 | 2 | 3 | 4 | 5 | 6 | 7 |
|---|---|---|---|---|---|---|---|---|
| Premix phase | Pal-GH | 0.6 | 0.6 | 0.6 | 0.6 | 0.6 | 0.6 | 0.6 |
| | 1,2-Hexanediol | 2 | 2 | 2 | 2 | 2 | 2 | 2 |
| | Stearic acid | | 0.06 | 0.06 | 0.06 | 0.06 | 0.06 | 0.06 |
| | Water | 2.4 | 2.34 | 2.34 | 2.34 | 2.34 | 2.34 | 2.34 |
| Aqueous phase | Ascorbic acid | 10 | 5 | 5 | 10 | 10 | 5 | 10 |
| | Glycerin | 50 | 50 | 20 | 50 | 20 | | |
| | Water | 35 | 40 | 70 | 35 | 65 | 90 | 85 |
| | Total | 100 | 100 | 100 | 100 | 100 | 100 | 100 |
| | Viscosity (mPa · s) | 480 | 444 | 33 | 416 | 69 | 19 | 25 |

| Phase | Composition | 8 | 9 | 10 | 11 |
|---|---|---|---|---|---|
| Premix phase | Pal-GH | 0.6 | 0.6 | 0.6 | 0.6 |
| | 1,2-Hexanediol | 2 | 2 | 2 | 2 |
| | Stearic acid | 0.06 | 0.06 | 0.06 | 0.06 |
| | Water | 2.34 | 2.34 | 2.34 | 2.34 |
| Aqueous phase | Ascorbic acid | 5 | 5 | 10 | 10 |
| | BG | 20 | 10 | 20 | 10 |
| | Water | 70 | 80 | 65 | 75 |
| | Total | 100 | 100 | 100 | 100 |
| | Viscosity (mPa · s) | 76 | 33 | 156 | 52 |

Example 12 to Example 21

Preparation 2 of Ascorbic Acid Thickened Composition

Compositions 12 to 21 shown in Table 2 were prepared by the following procedure.

Components of a premix phase were weighed according to the amounts thereof to be added shown in Table 2, into a sample tube No. 5 (manufactured by Maruemu Corporation). Components of an aqueous phase were also weighed according to the amounts thereof to be added shown in Table 2, into a 300-mL tall beaker. Then, the premix phase and the aqueous phase were heated to not lower than 70° C., respectively. The premix phase and the aqueous phase were mixed, followed by stirring to cool. Stirring was stopped when the temperature of the liquid reached 40° C., and, thus, a composition sample was prepared.

The viscosity of the sample thus prepared was measured with a viscometer (AND VIBRO VISCOMETER SU-1A). The value of the viscosity used was the one measured 1 minute after vibration was applied. The results are shown in Table 2. In Table 2, Pal-GH refers to the lipid peptide obtained in Synthesis Example 1 (free form of N-palmitoyl-Gly-His), and BG refers to 3-butylene glycol.

TABLE 2

Amounts of components to be added, in 100 g of ascorbic acid thickened composition (Example 12 to Example 21)

| Phase | Composition | 12 | 13 | 14 | 15 | 16 | 17 |
|---|---|---|---|---|---|---|---|
| Premix phase | Pal-GH | 0.5 | 0.5 | 0.5 | 0.5 | 0.5 | 0.5 |
| | Polyoxyethylene lauryl ether | 0.4 | 0.4 | 0.4 | 0.4 | 0.4 | 0.4 |
| | 1,2-Hexanediol | 0.2 | 0.2 | 0.2 | 0.2 | 0.2 | 0.2 |
| | Stearic acid | 0.05 | 0.05 | 0.05 | 0.05 | 0.05 | 0.05 |
| | Water | 3.85 | 3.85 | 3.85 | 3.85 | 3.85 | 3.85 |
| Aqueous phase | Ascorbic acid | 5 | 5 | 10 | 10 | 5 | 10 |
| | Glycerin | 50 | 20 | 50 | 20 | | |
| | Water | 40 | 70 | 35 | 65 | 90 | 85 |
| | Total | 100 | 100 | 100 | 100 | 100 | 100 |
| | Viscosity (mPa·s) | 82 | 26 | 114 | 43 | 12 | 14 |

| Phase | Composition | 18 | 19 | 20 | 21 |
|---|---|---|---|---|---|
| Premix phase | Pal-GH | 0.5 | 0.5 | 0.5 | 0.5 |
| | Polyoxyethylene lauryl ether | 0.4 | 0.4 | 0.4 | 0.4 |
| | 1,2-Hexanediol | 0.2 | 0.2 | 0.2 | 0.2 |
| | Stearic acid | 0.05 | 0.05 | 0.05 | 0.05 |
| | Water | 3.85 | 3.85 | 3.85 | 3.85 |
| Aqueous phase | Ascorbic acid | 5 | 5 | 10 | 10 |
| | BG | 20 | 10 | 20 | 10 |
| | Water | 70 | 80 | 65 | 75 |
| | Total | 100 | 100 | 100 | 100 |
| | Viscosity (mPa·s) | 30 | 20 | 37 | 24 |

Comparative Example 1

Components shown in Table 3 except for ascorbic acid were weighed into a 300-mL tall beaker, followed by pH adjustment to pH7. Thereto, ascorbic acid was added, and the resultant mixture was heated in a water bath set at 75° C. for dissolution. When ascorbic acid dissolved, cooling was started with stirring. Stirring was stopped when the temperature of the liquid reached 40° C., and, thus, a composition sample was prepared. The viscosity of the sample thus prepared was measured with a viscometer (AND VIBRO VISCOMETER SU-1A). The value of the viscosity used was the one measured 1 minute after vibration was applied. The results are shown in Table 3.

TABLE 3

Amounts of components to be added, in 100 g of ascorbic acid thickened composition (Comparative Example 1)

| Composition | Comparative Example 1 |
|---|---|
| 2 wt % Hiviswako 103 aqueous solution | 12.5 |
| Ascorbic acid | 10 |
| 0.1M Aqueous NaOH solution | 5 |
| Glycerin | 50 |
| Water | 22.5 |
| Total | 100 |
| Viscosity (mPa·s) | 18 |

The invention claimed is:

1. A thickened composition, comprising:
   a polyhydric alcohol;
   water;
   an organic acid;
   at least one fatty acid;
   at least one surfactant; and
   a lipid peptide-type compound containing at least one of a compound represented by Formula (1) below and a pharmaceutically usable salt of the compound of Formula (1):

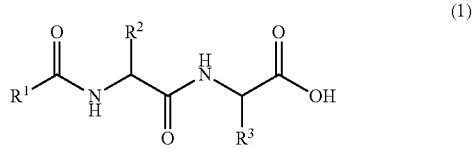

where:
   $R^1$ is a $C_{9-23}$ aliphatic group,
   $R^2$ is a hydrogen atom or a $C_{1-4}$ alkyl group that optionally has a $C_{1-2}$ branched chain,
   $R^3$ is a —$(CH_2)_n$—X group,
   n is a number of 1 to 4,
   X is an amino group, a guanidino group, a —$CONH_2$ group, a 5-membered ring group optionally containing 1 to 3 nitrogen atom(s), a 6-membered ring group optionally containing 1 to 3 nitrogen atom(s), or a condensed heterocycle group that contains a 5-membered ring and a 6-membered ring optionally containing 1 to 3 nitrogen atoms.

2. The thickened composition according to claim 1, wherein the fatty acid is stearic acid.

3. The thickened composition according to claim 1, wherein the surfactant is one or more compound(s) selected from the group consisting of ethylene glycol alkyl ethers.

4. The thickened composition according to claim 1, wherein the organic acid is ascorbic acid.

5. A feedstock premix for preparation of a thickened composition, the feedstock premix comprising:
   a polyhydric alcohol;
   water;

at least one fatty acid;
at least one surfactant; and
a lipid peptide-type compound containing at least one of a compound represented by Formula (1) below and a pharmaceutically usable salt of the compound of Formula (1):

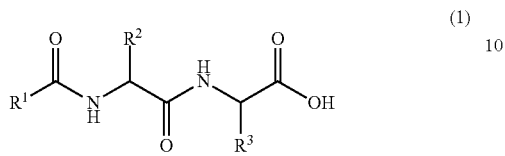

(1)

where:
R$^1$ is a C$_{9-23}$ aliphatic group,
R$^2$ is a hydrogen atom or a C$_{1-4}$ alkyl group that optionally has a C$_{1-2}$ branched chain,
R$^3$ is a —(CH$_2$)$_n$—X group,
n is a number of 1 to 4,
X is an amino group, a guanidino group, a —CONH$_2$ group, a 5-membered ring group optionally containing 1 to 3 nitrogen atom(s), a 6-membered ring group optionally containing 1 to 3 nitrogen atom(s), or a condensed heterocycle group that contains a 5-membered ring and a 6-membered ring optionally containing 1 to 3 nitrogen atoms.

* * * * *